(12) United States Patent
Stewart

(10) Patent No.: US 6,837,096 B2
(45) Date of Patent: Jan. 4, 2005

(54) LOW-POWER GAS CHROMATOGRAPH

(75) Inventor: Douglas C. Stewart, Mission, KS (US)

(73) Assignee: Midwest Research Institute, Inc., Kansas City, MO (US)

( * ) Notice: Subject to any disclaimer, the term of this patent is extended or adjusted under 35 U.S.C. 154(b) by 23 days.

(21) Appl. No.: 10/248,493

(22) Filed: Jan. 23, 2003

(65) Prior Publication Data
US 2004/0144159 A1 Jul. 29, 2004

(51) Int. Cl.[7] .................. G01N 30/02; G01N 30/04
(52) U.S. Cl. ............... 73/23.35; 73/23.36; 73/23.41
(58) Field of Search .................. 73/23.35, 23.36, 73/23.41, 23.42

(56) References Cited

U.S. PATENT DOCUMENTS

| 5,014,541 A | 5/1991 | Sides et al. |
| 5,099,743 A * | 3/1992 | Rounbehler et al. ........... 86/50 |
| 5,141,532 A | 8/1992 | Sacks et al. |
| 5,153,673 A | 10/1992 | Amirav |
| 5,268,302 A * | 12/1993 | Rounbehler et al. .......... 436/96 |
| 5,300,758 A | 4/1994 | Rounbehler et al. |
| 5,465,607 A | 11/1995 | Corrigan et al. |
| 5,611,846 A | 3/1997 | Overton et al. |
| 5,686,656 A | 11/1997 | Amirav et al. |
| 5,804,701 A * | 9/1998 | Berger ....................... 73/23.42 |
| 5,846,292 A | 12/1998 | Overton |
| 5,856,616 A * | 1/1999 | Maswadeh et al. ........ 73/23.42 |
| 5,922,106 A | 7/1999 | Mowry et al. |
| 6,209,386 B1 | 4/2001 | Mustacich et al. |
| 6,223,584 B1 | 5/2001 | Mustacich et al. |
| 6,306,200 B1 * | 10/2001 | Yu .............................. 96/102 |
| 6,351,983 B1 * | 3/2002 | Haas et al. ................. 73/23.37 |
| 6,386,014 B1 * | 5/2002 | Butch ........................ 73/23.35 |
| 6,612,153 B2 * | 9/2003 | White et al. ............... 73/23.42 |

* cited by examiner

Primary Examiner—Michael Cygan
(74) Attorney, Agent, or Firm—Blackwell Sanders Peper Martin LLP

(57) ABSTRACT

A low-power gas chromatograph is provided including an optional air sampler module, an injector, an analytical column, a pulsed-flame photometric detector, and a computer system. The gas chromatograph of the present invention is designed for portable use such that the sensitive components of the system are mounted in a way that they are at least partially insulated against shock applied to the instrument. A rugged housing is provided such that the instrument can be used during field operations without destruction of sensitive components due to dropping and the like.

20 Claims, 10 Drawing Sheets

LOW-POWER GAS CHROMATOGRAPH

The U.S. Government has a paid-up license in this invention and the right in limited circumstances to require the patent owner to license others on reasonable terms as provided for by the terms of Contract No. DSWA01-98-D-0126 awarded by the Defense Threat Reduction Agency.

BACKGROUND OF INVENTION

This invention relates generally to the field of gas chromatographs and, more specifically, to a portable low-power gas chromatograph.

Gas chromatography has long been used as an analytical technique for the identification and quantification of individual chemical compounds within a sample. A gas chromatograph is an analytical instrument that separates a gaseous sample (or a sample that has been converted to a gaseous state) into its constituent components. A typical gas chromatograph includes an injector that converts samples to a gaseous state (if needed) and moves the gaseous sample to the head of an analytical column in a narrow band; an analytical column, typically a long, coiled tube or the like, that separates the sample into its constituent components; a detector that detects and measures the constituent components as they emerge from the analytical column; and a data display for displaying the results of the analysis to a user. The constituent components of the sample are separated in the analytical column due to differential interactions between the components and an immobilized liquid or solid material within the column.

A typical gas chromatograph is heavy and not easily transported for use in the field. Light-weight, portable gas chromatographs are needed for a number of reasons. One such need is for support of required chemical analysis under the Chemical Weapons Convention (CWC). Under the CWC, there must be onsite analysis of samples during a three-day challenge inspection of a location. Sample analysis using the approved CWC gas chromatograph/mass spectrometer can take 45 to 90 minutes, thereby limiting the number of samples that can be analyzed. An instrument capable of quickly screening collected samples would greatly reduce sample analysis backlog under the CWC.

In addition, personnel conducting inspections for the CWC must enter various military and commercial facilities where highly dangerous chemicals may be present. A portable gas chromatography system provides the ability to maximize worker safety by sampling and analyzing the air at a location within a matter of minutes. A gas chromatography system that is capable of operating from a battery pack, has a self-contained gas supply, and is easily portable by one person could be used for such onsite monitoring.

Since the events of Sep. 11, 2001, the need for a portable, lightweight gas chromatograph capable of selectively detecting low and mid-levels of chemical warfare agents is a high priority. Such a device is needed to fill the gap between the gross-level hand-held detectors and the fixed-site continuous monitors used at military installations. Such a device could, among other things, be used to define the boundaries of a chemical incident, monitor the direction, speed and dissipation of a poison gas, monitor entry into an unknown area or environment, and provide near real-time monitoring and alarm at the scene of an incident.

A number of instruments potentially competitive with the low-power gas chromatograph of the present invention are currently available or under development in commercial and military markets. Each of these devices, however, has some limitation that is overcome by the present device. The available systems are divided into three categories and are discussed below.

Fixed Installation Instruments. This category is dominated by the Automatic Continuous Air Monitoring System (ACAMS), produce by ABB Process Analytics, and the MINICAMS, produced by CMS Research (U.S. Pat. Nos. 4,805,441 and 5,014,541). Both instruments are similar in operation and system design and both use a solid adsorbent collection media and a GC column wrapped around an aluminum mandrel for heating. The MINICAMS has multiple detector modules, including a pulsed-flame photometric detector, that can be exchanged to allow for detection of various compounds.

These instruments are not designed to be mobile air monitors, although both have been used as such after installing them onto trucks or vans. Instead, they were designed to continuously monitor a fixed location and sound an alarm if chemical agents are detected. Neither instrument has an onboard gas or power supply, both require AC line current and are extremely heavy.

Gross or High Level Instruments. Many gross level detectors are commercially available and supplied by several manufacturers. Most of these instruments use ion mobility spectrometry (IMS) as a detection mechanism and are capable of detecting chemical agents in the low ppm or high ppb concentration ranges. These instruments are handheld and battery powered. They required 0.5 to 2 minutes for chemical agent detection and provide a yes/no type answer as to the presence of an agent at concentrations where immediate health risks exist. They are not sufficiently sensitive to indicate whether a concentration of chemical agent exists at levels where mid or long-term exposure presents a health risk.

MINI GC. There are several portable GC systems that are currently available or in the prototype phase of development. Manufacturers include SRI International, Agilent, Analytical Specialist Inc., and RVM Scientific, Inc. Analytical Specialist, Inc., for example, is marketing the Microfast GC (U.S. Pat. No. 5,611,846). This device uses column technology that is similar to that used in the low-power gas chromatograph of the present invention. The Analytical Specialist device, however, uses a thermal conductivity detector, which does not provide sufficient sensitivity or selectivity for purposes of the present invention.

RVM Scientific has developed a beta portable GC (U.S. Pat. No. 6,223,584) that does use a pulsed flame photometric detector and analytical GC column, however the device currently lacks the ruggedness required to make it acceptable for a wide range of field uses. The device also has limited utility as a laboratory instrument for analysis of injectable samples and lacks the capacity to provide continuous air monitoring. The patent also discloses a significant limitation with the design in that the GC system has a leak rate of 0.1 mL/min.

Other gas chromatographs produced by Agilent and SRI are designed for laboratory operation and are not capable of air sampling without modification or addition of second party equipment being added.

The low-power gas chromatograph of the present invention addresses these and other concerns as outlined below.

SUMMARY OF INVENTION

The present invention provides a portable low-power gas chromatograph (LPGC) that overcomes the problems and limitations in the art. The LPGC of the present invention is constructed having a weight of about 30 pounds, with an upper weight limit of 42 pounds.

The GC components of the present invention, such as the air sampler, injector, transfer lines, column and detector, are provided in the design of the system with shock abatement so that damage due to dropping or other rough handling of the device is minimized.

The present device allows injection of liquid samples as well as an air-sampling module that operates as a near real-time monitoring instrument or as a point-source air sampler.

The present device is further designed such that the user is afforded easy access to the GC components that require periodic maintenance (primarily the air collection tubes, injector, and the column). Gas bottle exchange and battery replacement is possible while the user is wearing fully encapsulated Level A personal protective equipment (PPE).

The present device includes a display and a membrane switch keypad with error indicators that allow the user to view instrument parameters, view real-time chromatograms, and review experimental results.

The present device is operable via battery power or AC line current using an external AC-DC converter. The device is designed to sense whether the power source is the battery or AC line current and adjust itself appropriately.

Battery change-out or hot-swap is accomplished without loss of instrument operation. Battery charging is done off-line.

The present device is provided with its own source of hydrogen, air and helium gas supplies and is also able to access external gas supplies. The instrument is able to continue operating during exchanges between external and internal gas supplies.

The present device is provided with an audio and visual alarm that indicates alarm level concentrations of target compounds.

One embodiment of the present invention provides a dual column/detector arrangement such that the device is able to perform self-confirmation of experimental results.

DETAILED DESCRIPTION

One embodiment of the present invention includes a plurality of components and subsystems described below, including an air sampler module (for use when the device is used to directly sample the ambient air), an injector, a column, a pulsed flame photometric detector (PFPD), a PFPD tuning system, a housing, components for use in shock abatement, components designed to supply battery power to the device or deliver AC line current thereto, and a gas container/supply system. Also provided are various components for heating specified components and/or subsystems of the present invention, as well as computer and electronic components designed to facilitate user interaction with the device as well as analysis and presentation of experimental results. The details of each of these components and/or subsystems described below are exemplary and it is contemplated that variations on what is described may be used without departing from the spirit or scope of the invention.

Figure 1:
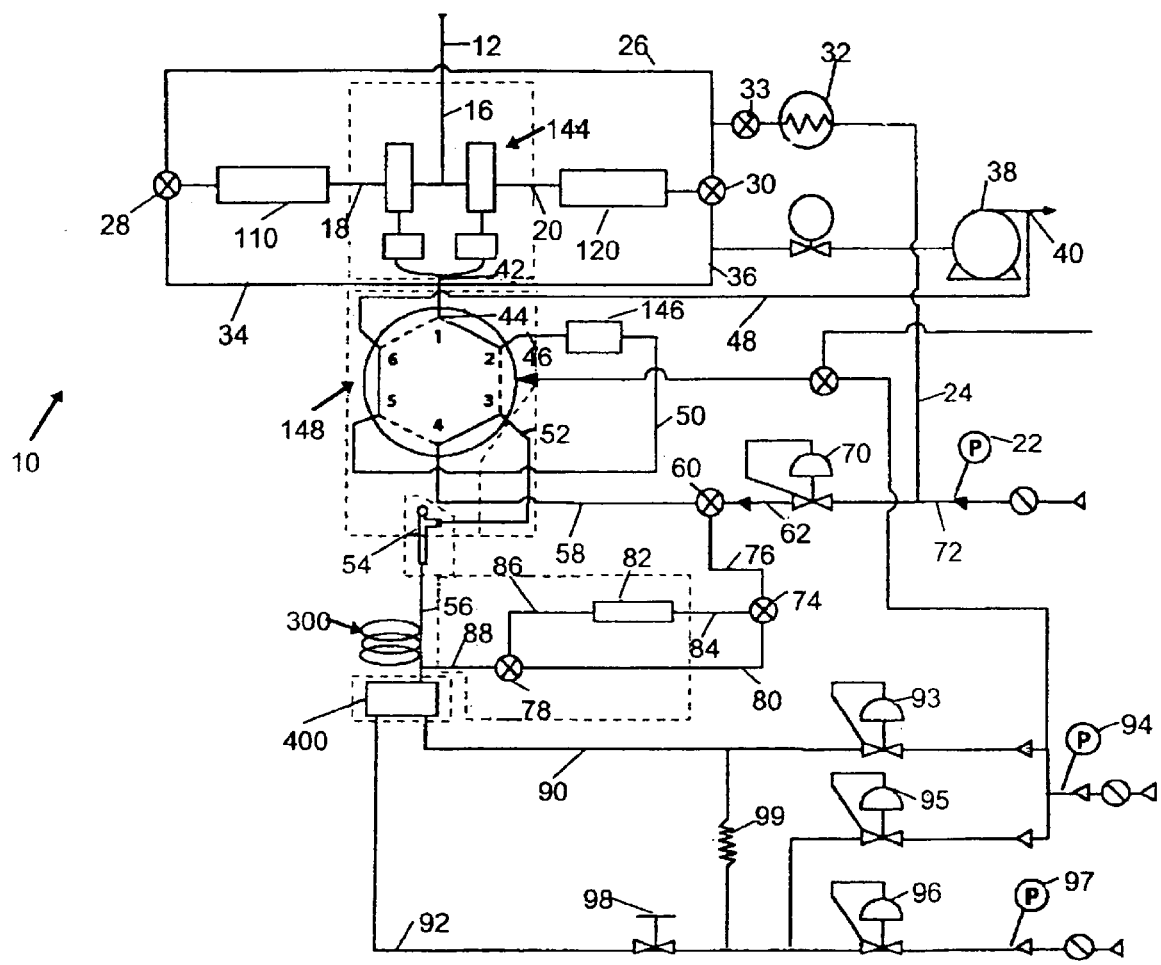
FIG. 1 is a schematic illustration of a low-power gas chromatograph constructed in accordance with the teachings of the present invention.

FIG. 1 provides a schematic illustration of one embodiment of a low-power gas chromatograph, designated generally by the numeral 10, constructed in accordance with the teachings of the present invention. The device has a sample inlet 12 connected to a four-valve manifold 144 via an inlet/outlet line 16 (inlet/outlet lines are hereinafter referred to as "lines"). Two collection tubes 110 and 120 are connected to four-valve manifold 144 via lines 18 and 20, respectively. A pressure regulator 22 provides helium from a helium source (not shown) via first helium lines 24 and 26 to collection tubes 110 and 120. Three-way valve 28 must be open for helium supplied by the pressure regulator 22 to reach collection tube 110, and three-way valve 30 must be open for helium pumped by pressure regulator 22 to reach collection tube 120. In a preferred embodiment of the present invention, a flow restrictor 32 is used to regulate the flow of helium along helium lines 24 and 26.

Air from the sample inlet 12 is provided to collection tube 110 when three-way valve 28 is opened to provide connection between collection tube 110 and vacuum line 34. Air from sample inlet 12 is provided to the collection tube 120 when three-way valve 30 is opened to provide connection between collection tube 120 and exhaust line 36. Exhaust lines 34 and 36 are connected to a vacuum pump 38 that draws the exhaust through vent 40 and expels it to the interior of the instrument for evacuation by an exhaust fan (not shown).

Line 42 of four-valve manifold 144 connects to line 44 of port one of six-port valve 148. Line 46 connects port two of six-port valve 148 to a first end of focusing tube 146. Line 50 connects a second end of focusing tube 146 to port five of six-port valve 148. Line 48 connects port six of six-port valve 148 to vent 40. Line 52 connects port three of six-port valve 148 to liquid injection port 54 Line 56 is an extension of the analytical column to the injector which in turn is directly connected to analytical column 300. Line 58 connects a port four of six-port valve 148 to three-way valve 60. Three-way valve 60 is connected via line 62 to a flow controller with flow meter feedback 70. Flow controller with flow meter feedback 70 is connected to pressure reducer 22 and the helium source (not shown) via line 72.

Three-way valve 60 is connected to three-way valve 74 via line 76. Three-way valve 74 is, in turn, connected to three-way valve 78 via line 80. Three-way valve 74 is connected to a first end of permeation tube 82 via line 84, and three-way valve 78 is connected to a second end of permeation tube 82 via line 86. Three-way valve 78 is connected to analytical column 300 and pulsed-flame photometric detector (PFPD) 400 via line 88.

Connected to PFPD 400 are air line 90 and combination air/hydrogen line 92. Air line 90 is connected to flow controller with flow meter feedback 93 which, in turn, is connected to pressure reducer 94 and an air source (not shown). Combination air/hydrogen line 92 is connected to flow controller with flow meter feedback 95, which is connected to pressure reducer 94 and an air source (not shown), and flow controller with flow meter feedback 96, which is connected to pressure reducer 97 and a hydrogen source (not shown). Combination air/hydrogen line 92 is also connected to a fine adjust valve 98. Air line 90 and combination air/hydrogen line 92 are connected by restrictor tube 99.

Figure 2:
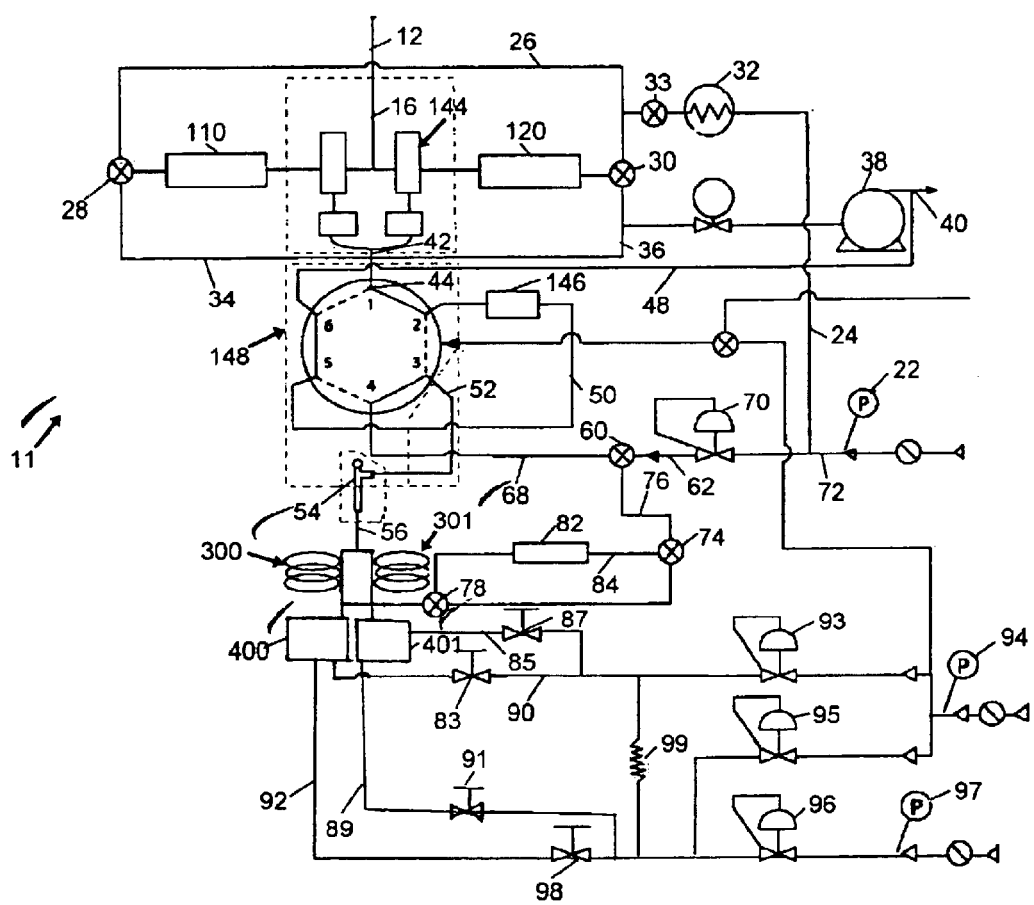
FIG. 2 is a schematic illustration of an alternative embodiment of a low-power gas chromatograph constructed in accordance with the present invention having a dual column/detector configuration of self-confirmation of analytical results.

FIG. 2 provides a schematic illustration of one alternative embodiment of a low-power gas chromatograph, designated generally by the numeral 11, constructed in accordance with the teachings of the present invention. The device is largely the same as the embodiment shown in FIG. 1. The key difference between the two embodiments lies in the fact that, in this alternative embodiment of the present invention, two analytical columns are present. The device includes analytical column 300 of the first embodiment of the present invention, described above, as well as an additional analytical column 301. Likewise, a second PFPD 401 is provided. In a preferred embodiment of the present invention, the stationary phase of analytical column 301 is different from that of analytical column 300. Connected to PFPD 401 are air line 85 and combination air/hydrogen line 89. Air line 85 is connected to fine adjust valve 87. Combination air/hydrogen line 89 is connected to fine adjust valve 91. Combination air/hydrogen line 89 is also connected to flow controller with flow meter feedback 95, which is connected to pressure reducer 94 and an air source (not shown), and flow controller with flow meter feedback 96, which is connected to pressure reducer 97 and a hydrogen source (not shown). Fine adjust valve 83 is present along line 90 to regulate gas flow to PFPD 400. Although a specific arrangement of flow lines and valves is provided in the figures, it is understood that one of ordinary skill in the art could practice the present invention using a different arrangement of flow lines and valves, adding or removing lines and valves, or changing the location of each, in a suitable manner.

The significance of this design is that the device is able to perform self-confirmation of analytical results. The system confirms results by comparing the results from the two column/detector systems. The results should match within experimental error limits. If the results do not match within such limits, the system determines that there is no "hit" and does not generate an alarm to signal the user of the presence of a target compound. Alternatively, if the results match within experimental error limits, the systems determines that there is a "hit" and generates an alarm to alert the user to the presence of the target compound.

Figure 3:
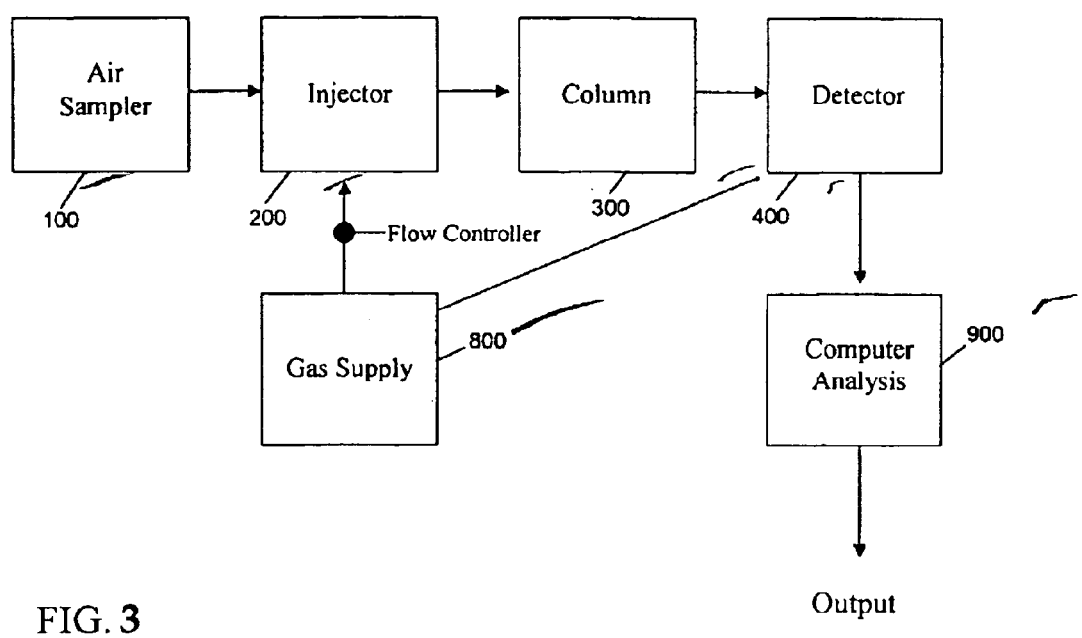
FIG. 3 is a block diagram showing the major subsystems of the low-power gas chromatograph of the present invention when the instrument is configured for one of its air sampling modes.
Figure 4:
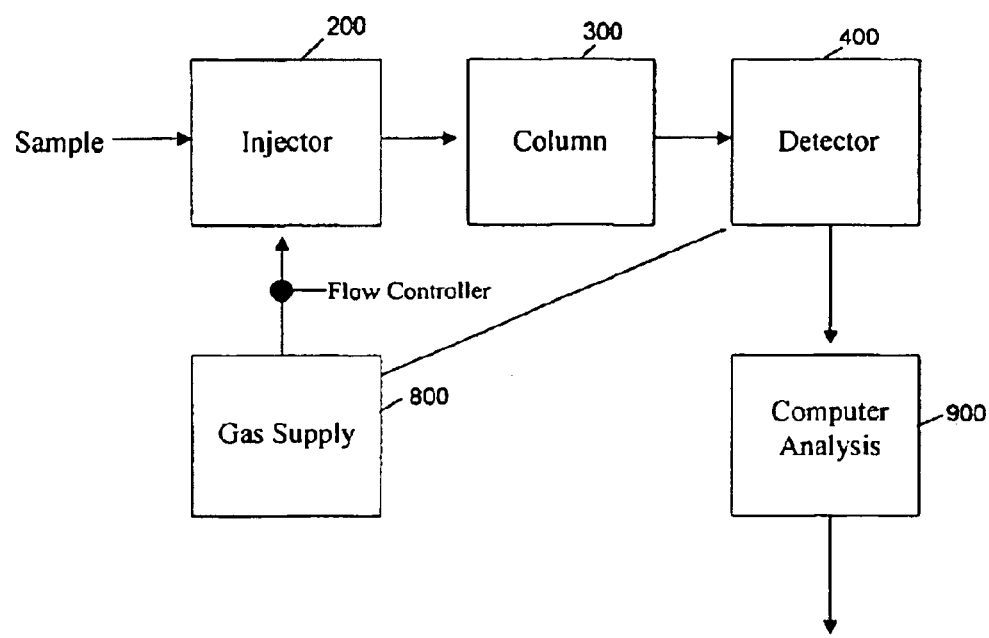
FIG. 4 is a block diagram showing the major subsystems of the low-power gas chromatograph of the present invention when the instrument is configured for its liquid injection mode.

It is contemplated that the present device can be operated in liquid injection mode or in one of two air sampling modes: 1) single air sampling mode; and 2) continuous air sampling mode. In either of the air sampling modes, an air sampler module 100 is required and active. If the device is being operated in liquid injection mode, air sampler module 100 is not required. FIG. 3 provides a simple block diagram of the layout of one embodiment of the present LPGC in air sampling mode. As can be seen from the diagram, air sampler module 100 is present. FIG. 4 provides a simple block diagram of the layout of another embodiment of the present LPGC in liquid injection mode. Air sampler module 100 is not powered or active in this instance. Present in both air sampling modes and liquid injection modes are the injector 200, the column 300, the detector 400, the gas container/supply system 800, and computer system 900. Each of these components and subsystems are described in greater detail below.

Air Sampler Air sampler module 100 is provided with the present invention for use when the LPGC is used to directly sample the ambient air. Air sampler module 100 is not used when the LPGC of the present invention is in the liquid injection mode of operation.

Any collection valves and transfer lines associated with air sampler module 100 that have the potential to come into contact with the target analytes must be heated to prevent the condensation of analytes onto the surfaces of the valves and lines. The temperature to which the valves and lines are heated is determined by the user, preferably being chosen from a range of 0° C. to about 175° C. with a maximum error limit of ±10° C.

Figure 5:
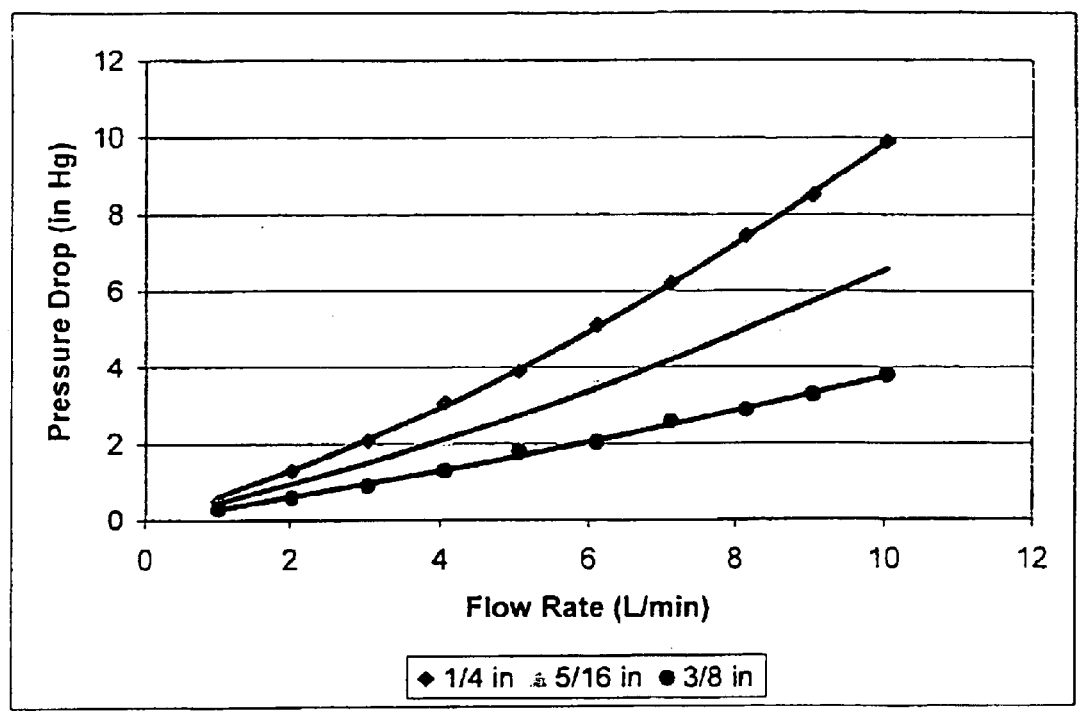
FIG. 5 is a graph depicting the pressure drop profile for various collection tube diameters.

Air sampler module 100 includes, in a preferred embodiment, collection tubes 110 and 120 (each of which contains a collection trap 133), which provide the capture mechanism for LPGC air sampler module 100. These tubes preferably have a large internal diameter and short adsorbent bed depth (from about 1 cm to about 3 cm) and a 1 cm bed depth to minimize the pressure drop across the tube and thereby minimize power requirements. In a preferred embodiment of the present invention, collection tubes 110 and 120 are able to collect sample at a minimum rate of 0.5 L/minute and may collect sample all the way up to about 8 L/minute. FIG. 5 is a graph showing the pressure drop profile for various collection tube diameters. The pressure drop across collection tubes 110 and 120 changes substantially with diameter, bed depth and flow rate.

Figure 6:
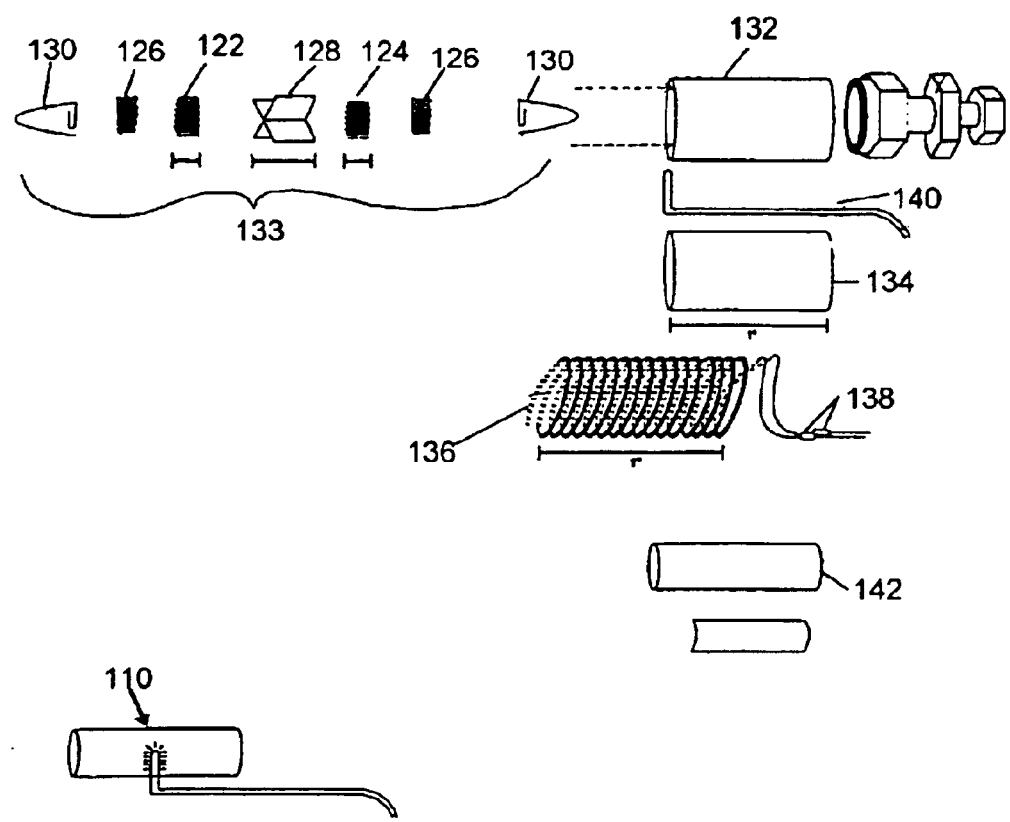
FIG. 6 is an exploded view of one embodiment of a collection tube constructed in accordance with the teachings of the present invention.

Collection tubes 110 and 120 are designed to collect relatively small volumes of air (from about 10 to about 100 liters) over a period of time ranging from about 1 to about 20 minutes. Larger collection volumes can lead to analyte breakthrough of some target compounds. The design of collection tubes 110 and 120 is shown in FIG. 6. In the interest of clarity, only one collection tube 110 is shown in the figure. The design shown, however, applies equally to collection tube 120. In a preferred embodiment of the present invention, collection tubes 110 and 120 are approximately 5/16 or 3/8-inch OD by 3 inches. The sorbent bed is approximately 1 to 3 cm long and contains equal layers of 60/80 mesh Tenax GR (indicated by numeral 122) and 60/80 mesh Chromosorb 106 (indicated by numeral 124). The bed is arranged such that Tenax GR 122 is the first to contact the air stream. Each of layers 122 and 124 are abutted by a layer of quartz wool 126. Between the layers, an X-shaped stainless steel heat exchanger 128 may be provided. The entire assembly (collection trap 133) is held together by retainer clips 130. Collection tubes 110 and 120 are capable of rapid heating to a uniform internal temperature. Because of this, performance is negatively affected by increasing OD. Thus, collection tube design achieves a compromise between power use and desorption time.

It is preferred that collection tubes 110 and 120 are made using a length of 316 stainless steel (SS) 132 wrapped with an appropriate high-temperature tape 134 for electrical insulation. Custom wire heater 136 constructed from 0.005 nichrome wire is wound over electrically insulated 316 SS tube 132 and cemented in place. Alternatively wire heater 136 may be bonded directly to the collection tubes 110 and 120. Connectors 138 are attached to wire heater 136 in order to provide power thereto. Wire heater 136 is covered with another layer of tape and thermocouple lead 140 is fixed along the length of tube 132. Lead 140 and connectors 138 are then covered with a final layer of tape 142. No thermal insulation is used since collection tubes 110 and 120 cycle over a wide range of temperature and require very fast heating and cooling. The heating range is from ambient temperature to about 250° C.

Collection tubes 110 and 120 are heated at a rate of from about 5° C. to 20° C. per second. The maximum desorption temperature allowed is about 250° C., with a maximum error limit of about ±15° C. Collection tubes 110 and 120 are cooled after desorption at a minimum average rate of about 100° C. per minute. Muffin fans (not shown) are positioned in close proximity to each of collection tubes 110 and 120 with a flow rate of ambient air from about 45 to about 140 liters per minute. In a preferred embodiment of the present invention, collection tubes 110 and 120 are designed such that replacement of collection trap 133 requires five minutes or less.

When the LPGC of the present invention is in continuous air sampling mode, collection tubes 110 and 120 alternate between collection cycles. The air to be sampled is diverted to either collection tube 110 or collection tube 120 by 4-valve manifold 144. The four-valve manifold 144 also serves to direct the sample from desorbed collection tube 110 or 120, as the case may be, to the focusing subsystem described below. The connections between collection tubes 110 and 120 and four-valve manifold 144 are insulated to allow efficient analyte collection during the collection cycle. The connections are also heated, as is four-valve manifold 144. The collection cycle is described here with reference back to FIG. 1. Air enters the system through sample inlet 12 and is directed to one of collection tubes 110 or 120 by four-valve manifold 144. For purposes of illustration, the figure will be described under the assumption that collection tube 110 has just collected its sample. Collection tube 110 then begins a desorption cycle and is closed with respect to the outside air by four-valve manifold 144. The desorption is accomplished, for example, with an ambient purge of from about 2 to about 10 seconds using helium at about 200 mL per minute. The purge is followed by rapid heating of collection tube 110 to desorb the collected analytes. During this time, the focusing tube 146 is in collect mode and is maintained at ambient temperature. While collection tube 110 is going through its desorption cycle, collection tube 120 begins its collection cycle. The air to be sampled is directed into collection tube 120 by four-valve manifold 144. As desorption of collection tube 110 is accomplished, the sample is directed to focusing tube 146 by a six-port valve 148. Further downstream, analytical column 300 is completing its previous analytical cycle, if any, and enters a cooling period.

Following desorption, collection tube 110 begins a cooling cycle with an ambient purge of from about 2 to about 20 seconds using helium at about 200 mL per minute. After the purge, helium flow is discontinued. Focusing tube 146, having collected sample desorbed from collection tube 110, is in desorb mode, which starts with a short purge and is followed by rapid heating, a short high-temperature hold and, finally, a cooldown. Analytical column 300 begins its analysis cycle when six-port valve 148 changes to provide flow from focusing tube 146 to analytical column 300. Collection tube 120 continues in its collection cycle.

Next, collection tube 120 completes its collection cycle and enters a desorption cycle identical to the desorption cycle described with respect to collection tube 110, above. The collection cycle is followed by rapid heating of collection tube 120 to desorb the collected analytes. During desorption of collection tube 120, focusing tube 146 is again in its collection cycle and is maintained at ambient temperature. Six-port valve 148 is positioned to allow sample flow from collection tube 120 and to prevent flow to analytical column 300. Collection tube 110 begins a new collection cycle while collection tube 120 is in its desorption cycle. Analytical column 300 is completing the previous analysis cycle and enters a cooling period.

After its desorption cycle is completed, collection tube 120 begins a cooling cycle identical to that described with respect to column 110, above. Focusing tube 146 is again in a desorption cycle and, when six-port valve 148 changes to allow flow from focusing tube 146 to analytical column 300, analytical column 300 begins a new analysis cycle. Collection tube 110 remains in collection mode. The process described above can be repeated for as long as continuous air sampling is required.

Focusing tube 146 provides compression of target analytes into a narrow band suitable for transfer onto analytical column 300. In one embodiment of the present invention, the focusing tube is 2⅜ inches long with a 1/16 inch OD. The sorbent bed is 0.8 to 1.5 inches deep and contains equal parts of Tenax GR and Chromosorb. It is contemplated that other solid adsorbents, such as HayeSep D, Carboxin 569, Tenax TA, CarboTrap C, or any other suitable solid adsorbent, may be used in place of Tenax GR and/or Chromosorb. The bed is arranged such that the Tenax GR is the first to contact the air stream. This assembly is also called the focusing trap.

Focusing tube 146 is made using a length of 316 stainless steel wrapped with an appropriate high temperature tape for electrical insulation. Custom wired heaters are constructed using nichrome wire wound over the electrically insulated tube and bonded in place. Alternatively, the heater may be bonded directly to focusing tube 146. No thermal insulation is used as the tube cycles over a wide range and requires rapid heating and cooling between ambient temperature and about 250° C. Cooling is accomplished using a muffin fan positioned in close proximity to the focusing tube and with an ambient air flow rate of approximately 50 liters per minute.

Connection tubing between focusing tube 146 and the four-port valve 144, as well as connections to the rest of the focusing subsystem, including the six-port valve 148, are insulated.

Any valves and transfer lines that have potential for contact with the target analytes must also be heated in the same manner as described with respect to the collection valves and transfer lines, above. Since focusing tube 146 functions to provide a mechanism for creating a narrow chromatograph analyte plug for introduction into the chromatographic system, the focusing tube is narrow in internal diameter and is adapted for rapid heating.

The focusing trap collects analyte from the collection tubes at a flow rate of from about 200 mL per minute to about 500 mL per minute. The focusing trap is desorbed at the flow rate of the column carrier gas.

Focusing tube 146 is heated at a rate of from about 5° C. per second to about 20° C. per second. The maximum desorption temperature allowed is about 250° C., with a maximum error limit of about ±15° C. Focusing tube 146 is cooled after desorption at a minimum average rate of about 100° C. per minute. Focusing tube 146 is designed such that replacement of the focusing trap takes about 10 minutes or less.

Air sampler module 100 also includes at least one pump 38 that is able to collect sample at flow rates sufficient to allow sampling at the current time-weighted average (TWA) concentration values. The pump also allows sampling at the proposed worker population limit (WPL) concentration levels. An example of the calculated flow rates for TWA and WPL collection of VX gas is shown in Table 1, below.

TABLE 1

Calculated Flow Rates for TWA and WPL Collection of VX Gas

|  | ng/mL | ng | Flow rate (mL/min) | Time (min) |
| --- | --- | --- | --- | --- |
| TWA | 0.00001 | 0.05 | 500 | 10.00 |
| TWA | 0.00001 | 0.05 | 2000 | 2.50 |
| TWA | 0.00001 | 0.05 | 3000 | 1.67 |
| TWA | 0.00001 | 0.05 | 4000 | 1.25 |
| TWA | 0.00001 | 0.05 | 5000 | 1.00 |
| WPL | 0.000001 | 0.05 | 1000 | 50.00 |
| WPL | 0.000001 | 0.05 | 2000 | 25.00 |
| WPL | 0.000001 | 0.05 | 3000 | 16.67 |
| WPL | 0.000001 | 0.05 | 4000 | 12.50 |
| WPL | 0.000001 | 0.05 | 5000 | 10.00 |

The collection flow rate is adjusted by a collection flow meter that is monitored by the computer which adjusts the power to the vacuum pumps and in a preferred embodiment, is user selectable between about 0.5 and 5 L per minute. Flow meter feedback is provided to enable the device to maintain the appropriate flow. The maximum user selectable error limit is about ±500 mL per minute. Flow rate is controlled by increasing the DC voltage to the pump(s). For flows up to about 3 liters per minute, only one pump 38 is required. In embodiments of the present LPGC having more than one pump, each pump 38 is individually switched so that the firmware can turn on an additional pump 38 and adjust the voltage supply accordingly when additional flow is required.

Helium is the carrier gas used for thermal desorption of trapped analytes from collection tubes 110 and 120. A critical orifice is used to provide helium flow at a rate of about 175 to about 250 mL per minute. The pressure required to establish critical flow is the minimum operating pressure for the system and must be electronically monitored. Helium flow timing control is provided by a shut-off valve 33.

Pump 38 is used in suction and are thus downstream of all collection system components. It is connected by flexible lines to the upstream system in order to minimize vibration transfer to the collection components and other LPGC subsystems. It is not necessary for pump 38 to be heated. It is preferred that air entering pump 38 not exceed 40° C. Pump 38 is exhausted inside the instrument case and removed by an exit fan away from the air inlet. Operating only one pump 38 at a time reduces power consumption when flows below about 3 liters per minute are required by the method selected.

Injector 200 is active for the liquid injection mode of operation as well as for both air sampling modes of operation. Injector 200 in preferably fabricated using a commercial-off-the-shelf (COTS) unit modified for the low-power application of the present invention. The body is a tow-volume injector designed for U.S. with purge-and-trap devices. Use of this injector allows for easy connection of the injector to the GC air sampling system. Suitable injectors are readily available commercially, for example from Restek (part number 21692).

Injector 200 is heated with a coiled tube heater that is used to heat the injector to an operating temperature of from about 200° C. to about 275° C. The temperature of injector 200 is user-selectable between a range of 0° C. to about 275°, with the desired operating temperature varying depending upon the precise use of the instrument. The degree of error in injector temperature is also user selectable but preferably does not exceed ±5° C. In a preferred embodiment of the present invention, the coiled tube heater used is a Watlow Quote #0232M093, or equivalent.

Injector 200 should be insulated in order to minimize heat loss in the system. Insulation is preferredly accomplished by wrapping injector 200 in an aerogel blanket of about 4.5 mm thickness. The blanket is, in turn, contained within and protected by a high-temperature polymer housing. Numerous polymers, such as Torlon, for example, may provide a suitable housing.

It is preferred that injector 200 be directly connected to analytical column 300 using a Swagelok fitting. Other means of connecting injector 200 to analytical column 300 may be used, however it is important that the connection be rigid because vibration between the parts may cause damage to the column. As will be discussed further below, the GC system of the present invention will be provided with a frame that is shock and vibration mounted to the main case, providing a rigid mounting for all subsystem components of the LPGC system, including injector 200, analytical column 300, detector 400, and air sampler module 100.

As the temperature of injector 200 must be maintained, it is important to provide a temperature feedback device. In a preferred embodiment of the present invention, temperature feedback is accomplished using an Omega thermocouple (part #TCGG-K-30-36) or equivalent, which is located on an external surface of injector 200. Other temperature feedback devices may be used that measure temperature in the range of 0° C. to about 300° C.

Column Analytical column 300 used in a preferred embodiment of the present invention is available from RVM Scientific, Inc. as a custom built device. A suitable column, for example, is a 1701 type, 20 meter long, free-standing column with adjustable extended column transitions on the inlet and outlet. A muffin fan with a flow rate of about 125 L/min is used to cool column 300.

Column 300 is preferably mounted on a rigid SS bracket. The bracket is insulated from the subframe but rigidly connected to it using insulated ceramic fasteners. Though the connects are rigid, they allow for adjustment of column 300 and the cooling fan so that the column inlet and exit lines can be trimmed and reused. An adjustment of up to 1 inch is preferred, and an adjustment of ½ inch should be provided in any event.

Column 300 is preferably connected directly to the bottom of injector 200 using a nut and vespel graphite ferrule. The column bracket does not support the inlet section of column 300 and the transition heater will pass through the bracket without contact in order to reduce heat loss. In one embodiment of the present invention, the transition heater used is a heater acquired from RVM Scientific, Inc.

A custom tube with welded right-angle tee transfer line for the introduction of permeation gas is used for the entrance to detector 400 (described below). This arrangement minimizes the number of connections needed and reduces heat loss. The lower extension of the tube is sized for convenient entry of the column outlet line with the heater, and for connection using a nut and vespel ferrule, similar to that used with injector 200. Custom-tailoring of the length of the heater by using multiple heater segments allows precise location of the GC outlet line within the custom tube. The heater segments include a primary heater and at least one short heaters (about, for example, 0.5 inches) that can be removed to allow for modification of the column extension length.

The free, or uncoiled, end of column 300 is heated by a small-diameter tube heater. In one embodiment of the present invention, the heater used is one acquired from RVM Scientific, Inc. Any other suitable heater may be used for this purpose, or in any other instance in which the present invention requires a heater.

Detector The PFPD detector 400 used in a preferred embodiment of the present invention is available as a non-standard part from OI Analytical, College Station, Tex. A second standoff tube and photomultiplier tube (PMT) mount is precision welded to the detector body. The PMT is mounted so that it is heat insulated from the body, since it is significantly affected by temperature.

Detector 400 is rigidly mounted to the GC subframe via bolts attached directly to the detector body. This allows for no motion between analytical column 300 and detector 400. Heat loss is reduced using low thermally conductive materials, such as high-temperature polymers or ceramics, in the mounting system.

Each PMT is mounted from a tube welded to the detector body. The tube is designed to minimize heat transfer to the PMT. The PMTs are supported from a rigid subframe to account for impulse effects of shock to the instrument.

Detector 400 is maintained at a temperature range of from about 200° C. to about 275° C., as specified by the particular method selected. Aerogel insulation is used, surrounded by a high-temperature polymer support shell, to reduce heat loss to the case environment.

The LPGC of the present invention further includes two ignitors, which are the subject of co-pending U.S. patent application Ser. No. 10/248,433. A 10-watt ignitor is preferably used when the present device is in laboratory mode running from AC power. This greatly increases the life of the ignitors of the present invention. A 2-watt ignitor is provided for use when in field mode. This results in power savings when the device is being used in the field. The 2-watt ignitor has a shorter life than the 10-watt ignitor since it is designed to achieve the same temperature as the 10-watt device using a smaller gauge wire. The ignitor is designed such that installation in the field is relatively easy.

Wound wire heaters, cartridge heaters or thin film heaters may be used to maintain temperature in the detector area. The specific heater used is first selected from that best able to conform to the temperature plan, and second base upon efficient energy usage.

Although pulsed-field photometric detector 400 is used in a preferred embodiment of the present invention, it is contemplated that various other suitable detectors could be used, such as flame ionization detectors, flame photometric detectors, photoionization detectors, ion mobility spectrometers, or any other suitable detector known in the art.

PFPD Tuning System

Figure 7:
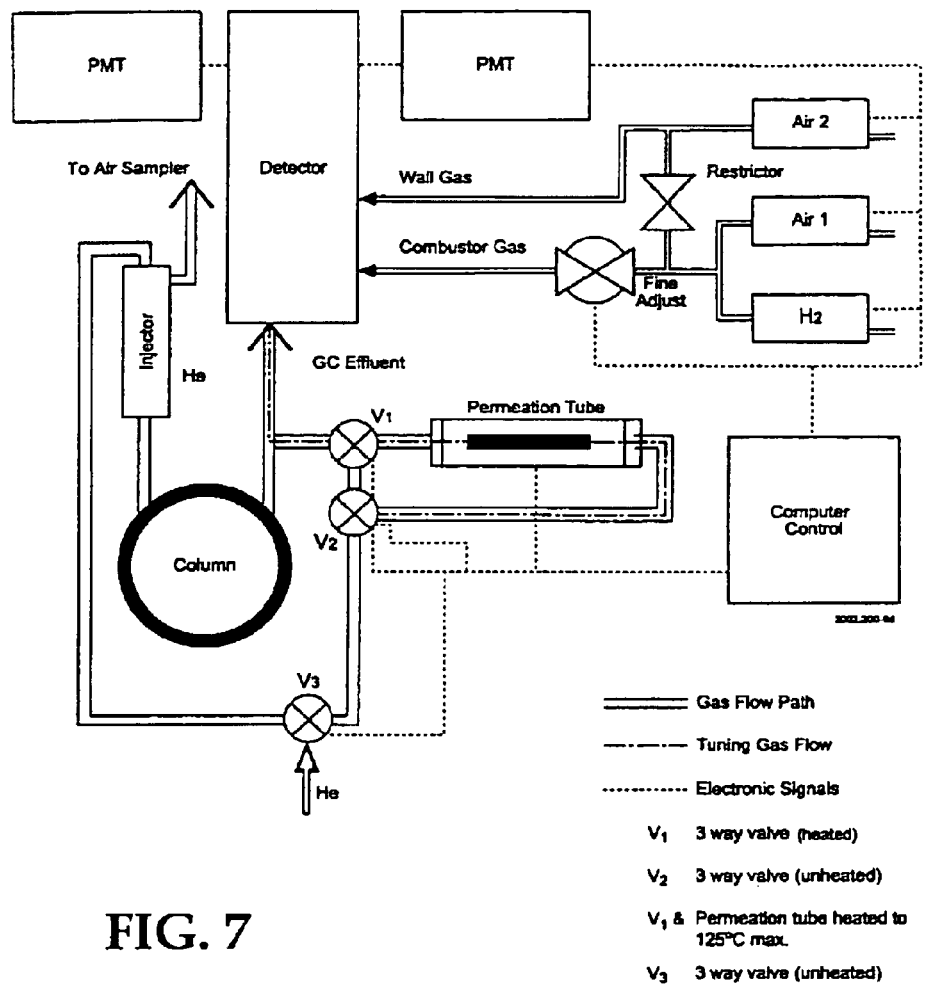
FIG. 7 is a schematic diagram of a PFPD tuning system constructed in accordance with the teachings of the present invention.

PFPD 400 requires tuning in order to maintain optimum sensitivity. The tuning system for PFPD 400 is the subject of co-pending U.S. patent application Ser. No. 10/248494. The instrument will perform an automatic tame of the detector when so commanded by the user. The following is an example of an automatic tuning process performed by the device. The example is provided as a series of steps for the sake of clarity. A schematic representation of one embodiment of the PFPD tuning system of the present invention is provided in FIG. 7. Example 1. Stepwise Procedure for Automatic Tuning of PFPD 400. 1. Verify that a non-fatal error does not exist. 2. Verify that helium flow rate is between 1 and 1.5 mL per minute. If the helium flow rate is not within this range, the software shall notify the user of the flow rate and ask to continue. 3. Verify that the detector block is at the appropriate temperature, which should be between 200° C. and 275° C. If the detector block is outside of this temperature range, the software shall notify the user of the temperature via a dialog box and ask to continue. 4. The software shall set the column temperature to ambient. 5. Apply power to tho stepper motors and flow meters. 6. Set the fine adjust valve to a position that is open two complete turns. 7. Set the hydrogen flow rate to 11.5 mL per minute. 8. Set the air 1 flow rote to 10 mL per minute. 9. Set the air 2 flow rate to 15 mL per minute. 10. Set the detector range to 10 volts. 11. If not on, apply power to the ignitor coil. The specific power requirement vanes depending on the ignitor used. 12. The software shall poll the device to test if the correct power level has been set. If the firmware has not set the power level the user shall be prompted. 13. Allow 30 seconds for the PFPD to begin pulsing. If pulsing does not occur, the user is prompted to cheek the system. 14. Allow 30 seconds for any erratic pulsing to subside. If the detector continues to pulse erratically, reduce hydrogen flow rate until pulsing becomes steady. If the pulsing does not become steady or the pulsing stops, prompt the user to check the system. 15. Verify that the system is pulsing at a rate between 3 and 4 Hz. If not, adjust air 2 accordingly. 16. Verify that the hydrogen-to-Air 1 flow ratio is approximately 1.15:1.0. 17. Slowly close the fine-adjust valve until the system goes into tick-tock (tick-tock is the combustion termination endpoint alternating between the top of the PFPD combustion). Once tick-lock has been achieved, open fine adjust valve ½ turn. 18. Open the valves to the permeation source. 19. Heat permeation tube to approximately 100° C. 20. Allow 5 minutes for sulfur diffusion to stabilize. 21. Monitor the width and amplitude of the sulfur response within the detector range. Increase or decrease the permeation source temperature to obtain a correct amplitude. 22. Verify that the emission is stable by monitoring the amplitude. It should not fluctuate by more than 20%. 23. Adjust the hydrogen flow rate between 9 mL per minute and 13 mL per minute in order to determine the effective width. 24. If the width of the emission extends to at least 21 ms (24 is preferred), the PFPD should be considered tuned and no further action is required. 25. If the width of the emission does not extend to 21 ms, decrease air 1 flow rate by 0.5 mL per minute. Monitor the effect of the change. 26. If there is no effect on the emission, continue to decrease air 1 flow rate in 0.5 mL per minute increments until a change is noticed. Allow 30 seconds between adjustments. 27. If the emission broadens, continue to decrease air 1 flow rate in 0.1 mL per minute increments until the emission readies or exceeds 24 ms. 28. If the emission does not broaden alter decreasing by a total of 5 mL per minute, or if the emission contracts alter a decrease, reset to the original 10 mL per minute flow rate for air 1. 29. Repeat the incremental process with air 1, except this time increase flow rate. 30. Once emission is broadened, check pulse frequency. Adjust air 2 to obtain a pulse rate between 3 and 4 Hz. If air 1 was decreased, increase air 2. If air 1 was increased, decrease air 2. 31. Slowly close (1/10 turn per second) the find-adjust valve until the system goes into tick-tock. Once tick-tack has been achieved, open the fine-adjust valve ½ turn. 32. Prompt the user that the tune is complete and request acceptance. 33. When user accepts, remove power from the stepper motors and flow meters. 34. Close valves to the permeation source. 35. Turn off heating to the permeation source. 36. Allow to cool for two minutes, then close the valves. 37. Monitor the emission and, when it has returned to zero or baseline, return user to MAIN screen. The permeation tube is preferably a ⅛-inch OD teflon tube filled with 1,4 Dithiane (CAS#505-29-3). This material is effective for PFPD tuning. The 1,4 Dithiane is depleted during multiple tuning operations and the permeation tube must ultimately be replaced. The permeation tube is maintained at a desired temperature by immersion in a heated well or tube. The line 88 from the permeation tube to the PFPD is also heated. Temperature control of the tubes, fines and valves is user enabled to a temperature of between 90° and 125° C.

Helium flow to the permeation tube is required at a rate of about 1.2 mL/minute. The flow rate is maintained using the helium flow controller used for column flow. An on/off control valve, similar to the latching three-way valves previously described, provide directional flow for the helium. The valve and the line to the permeation tube is not heated.

Laboratory replacement of the permeation tube is expected.

Housing Analytical column 300 (or analytical columns 300 and 301 in a dual column embodiment of the present invention), detector 400 (or detectors 400 and 401 in a dual detector embodiment of the present invention), injector 200, and air sample module 100 are components of what will be referred to herein as GC sub module 500. It is important to the operation of the present device that these components be insulated against shock to the device to the extent possible. To that end, the present device is provided with a housing 600 for enclosing GC sub module 500 therein. Housing 600 of the present device must be sufficiently durable to protect the LPGC during field operation. Approximate housing weights for possible construction materials is provided in Table 2 below. 6061 T6 aluminum and 7075 T6 aluminum are preferred due to their high strength-to-weight characteristics.

TABLE 2

Materials and Houseing Weights

| Material | Estimated wt. (lbs) |
| --- | --- |
| 316 stainless steel | 22.7 |
| 6061 T6 Aluminum or 7075 T6 Aluminum | 8.2 |
| Titanium 65-A | 13.6 |

Shock Abatement

The present device is intended to be portable and suitable for use in the field. Though the instrument is meant to be handled carefully due to its delicate nature, it is contemplated that some shock will occur in the field (as used herein, the term shock includes, but is not limited to, dropping the instrument, striking it with an object, or otherwise applying mechanical vibrations including sound thereto or, causing such vibrations to be transferred across the interior of the instrument, or any other force, whether generated internally or externally, that could affect the sensitive components of the LPGC). The GC elements must, therefore, be able to absorb some shock. Further, the connections between the GC column, which is only a few microns in diameter, and connecting parts requires rigidity. The design of the column and interconnecting components (GC sub module 500) provides a rigid structure that is mounted on isolation bushings in order to allow minimal shock to the case during transport and use, with no damage to the GC. The components to be so-mounted include injector 200, analytical column 300 (and analytical column 301, if present), detector 400 (and detector 401, if present) and air sampler module 100. As noted above, these components are part of GC sub module 500. Air sampler module 100 is mounted through the instrument case but is not rigidly attached. Since the present device is designed for use in portable mode using level-A personal protective equipment (PPE), the potential for drop/shock under field conditions must be accommodated.

Figure 10:
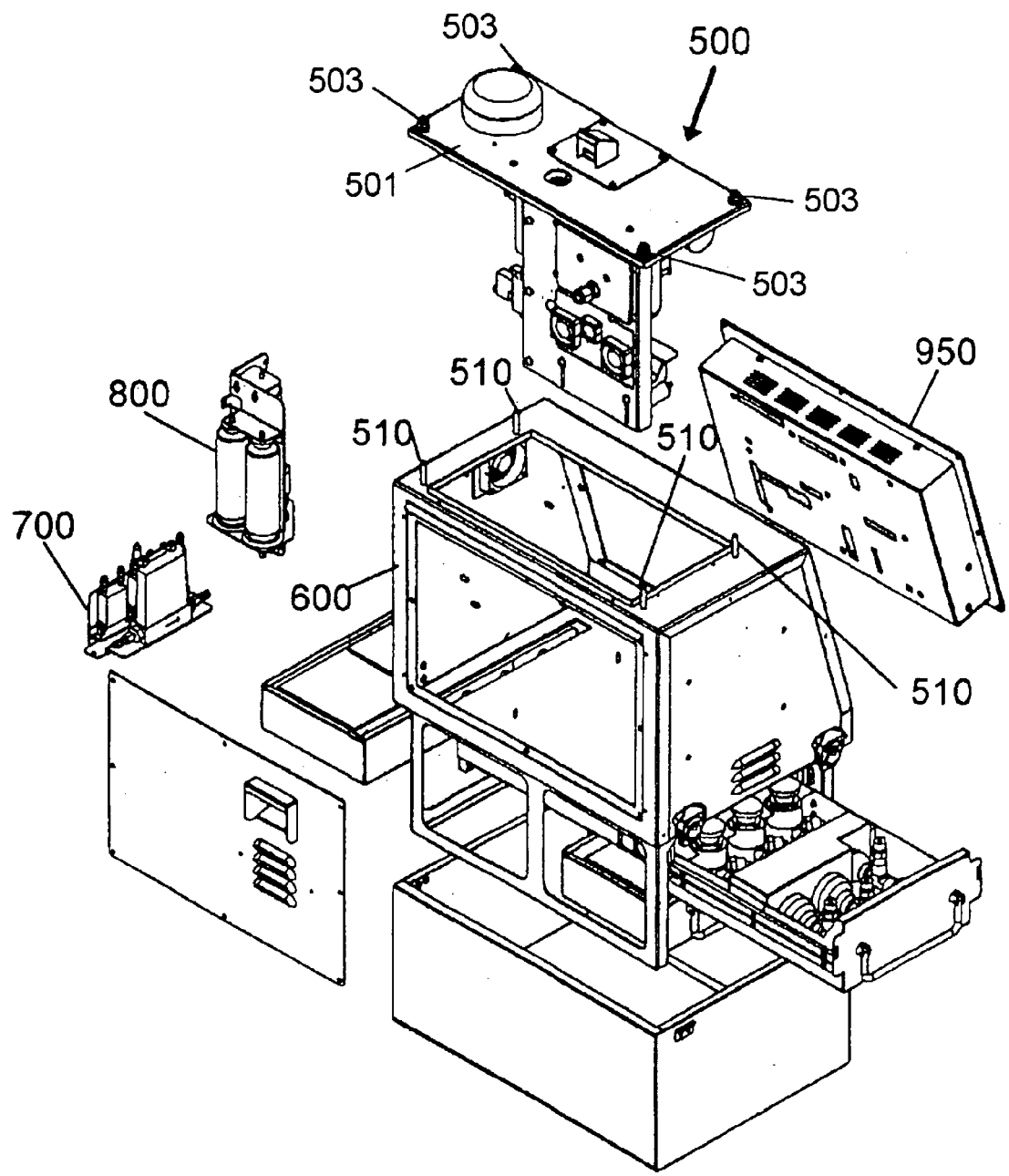
FIG. 10 is an exploded view of one embodiment of an LPGC of the present invention showing how the GC sub module fits within the housing.

GC sub module 500 of the LPGC is mounted on a rigid subframe secured to housing 600 via GC sub module securing pins 510. The subframe has shock mounts designed to transmit 10% or less of impulsive forces applied to the base of the instrument. This is accomplished by allowing GC sub module 500 to float within the device chassis. The only connection points are located on the very top of the device. These connection points are buffered using isolation bushings or insulators, or other suitable means. FIG. 10 provides an exploded diagram of one embodiment of an LPGC of the present invention showing how GC sub module 500 fits within housing 600, as described above.

Batteries

The present device is capable of running on battery 700 power and on 120 VAC, 60 cycle power. The device may also be operated on European power levels of 220 VAC, 50 cycle. It is preferred that the battery life is greater than 4 hours. Well-characterized rechargeable battery technologies such as Nickel Metal Hydride, Lithium Manganese Dioxide, and Lithium Ion (preferred) may be used.

Gas Container/Supply System

The present device includes a self-contained gas supply 800 for field use. In a preferred embodiment of the present device, an exchangeable cylinder drawer is used. In order to minimize unnecessary use of self-contained gas supply 800, the present device is adapted for use with standard gas cylinders when in a laboratory environment.

The present invention is designed such that the user is able to switch between self-contained gas supply 800 and the laboratory gas supply without shutting down the instrument. In addition, the on-board supply can be replaced without shutting down the instrument in portable mode.

Connection of the gas cylinders to the GC inlets is achieved using quick-connects from Swagelok. The drawer is designed using guide rails so that accurate alignment is assured without user sighting.

The present invention is designed such that gas supply 800 is sufficient for at least 4 hours of gas in continuous operation. For the embodiment having 4 hours of gas, a 50-mL tank of hydrogen is required at 1800 psi, a 150-mL tank of air is required at 1800 psi, and a 150-mL tank of helium is required at 1800 psi. These tanks can be readily obtained from Swagelok, with the corresponding part numbers being 304L-HDF4-50, 304L-HDF4-150, and 304L-HDF4-150, respectively.

A pressure regulator on each tank reports the tank pressure to the human interface. The tank pressure will be monitored. An error will be generated when this value is below a certain predefined level.

Computer System

Figure 8:
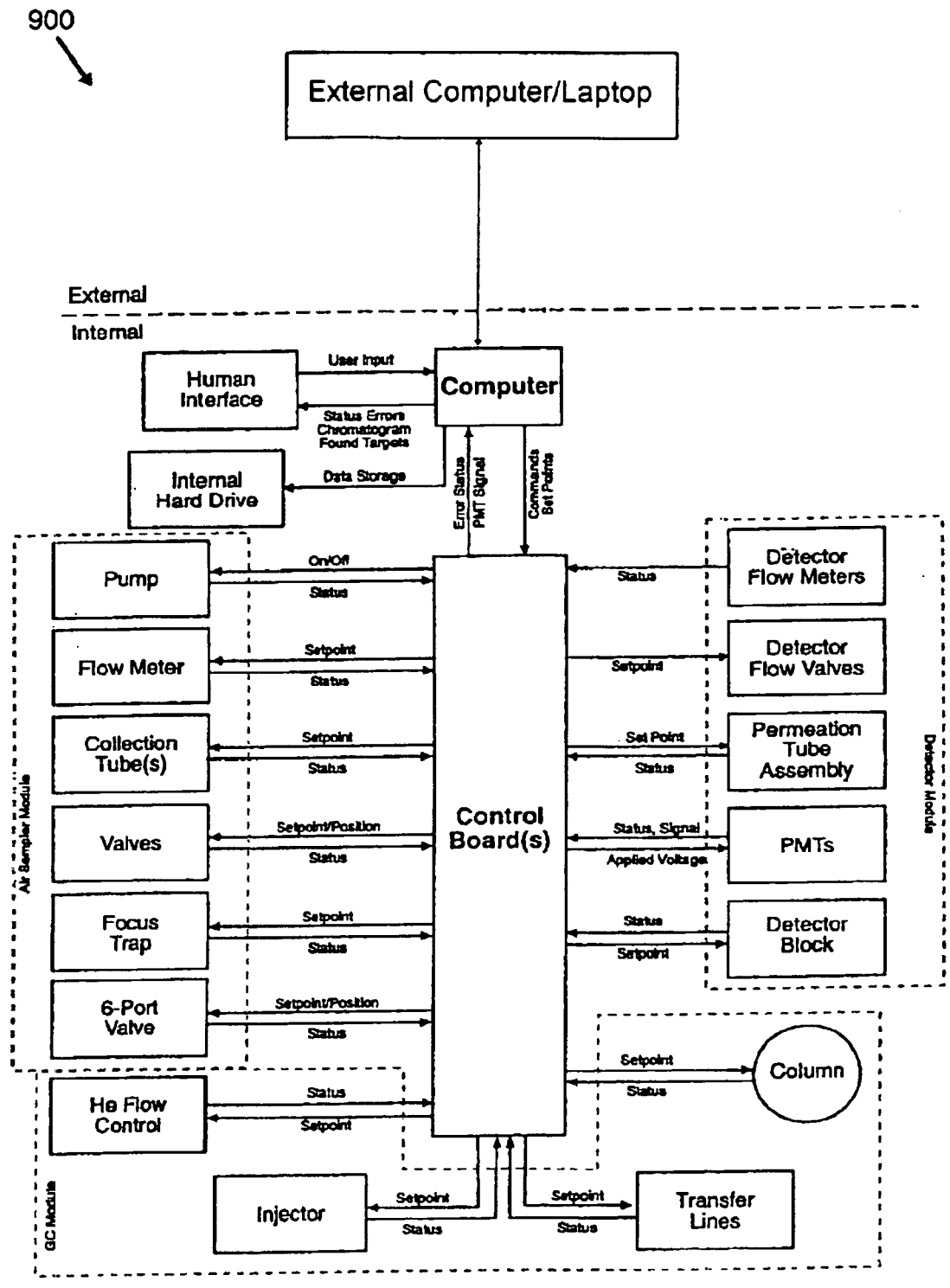
FIG. 8 is a block diagram of the computer system of one embodiment of a low-power gas chromatograph constructed in accordance with the teachings of the present invention.

The various components of the present LPGC are under the control of a computer system that also provides a user interface for the device. The computer system is designated generally by the numeral 900 in the accompanying drawings. FIG. 8 provides a schematic diagram of one embodiment of a computer system for the present LPGC. It is contemplated that those skilled in the art could develop various modifications to the computer system shown in FIG. 8, and to the system described below, without departing from the spirit and scope of the present invention.

In a preferred embodiment, the present invention includes a computer based on the Windows 2000 operating system. Certain minimum requirements must be met in order to run this operating system, however it is preferred that the single-board computer used by the present device exceed these requirements. For example, an Intel-compatible CPU running at a speed of at least 300 MHz is preferred, along with a 2 GB or greater capacity hard drive, at least 128 MB of RAM, at least one USB port and optional PCMCIA port, an ethernet port, and two or more COMM ports.

The primary human interface 550 to the computer system is the front panel of the LPGC. A numeric and special-function keypad is used for entry of information to the device. The display (preferably a LCD) provides visual feedback for the state of operation mode and all entries made by the user. A mouse or similar device is provided for additional functionality. The USB and/or PCMCIA port provides additional connectivity that expands human interface 550.

In the preferred embodiment human interface 550 and the computer pass commands to a subservient firmware processor that controls the actual hardware. This firmware processor monitors the hardware and reports back to the software the condition or status of the hardware.

In a preferred embodiment, a Hamamatsu R1924 PMT is used for a hardware control and monitoring board. The board is a rugged, low-profile, 25 mm diameter, Biaklali Photocathode (300 nm to 650 nm), 10 stage, head-on type. Each detector channel has a separate PMT and a separate filter in the optical pathway. Each PMT has a separate high-voltage power supply that will provide for independent adjustment of P and S channels. The high-voltage supply may be a C10N manufactured by Emco Corporation, which uses 11.5 to 16-VDC input and is programmable with 0 to 5-VDC to provide negative 0 to 1000 VDC, with less that 0.002% ripple under full load.

The signal of each channel is amplified and a secondary stage of programmable gain amplifier provides for selection of an optimum range. Offset adjustment controls are provided for each channel with negative position values. The user will be able to adjust for baseline shifts.

Signal from either the P or S channel is used to form a trigger pulse. It is preferred that the signal is from the P channel. The level of comparator circuit is programmable by the user. The trigger pules is used for control of the sampling with the analog to digital converter. The signal of each detector will be sampled at a minimum of 10 KHz.

The time windows (start and stop gates) are user-selectable for each detector channel and used for digital processing in the firmware. The temperature control for all heated zones are based on closed-loop heating. Separate channels are used, potentially with different temperature sensors. The most power-efficient heating techniques are used wherever practical. During cooling, the heater is off and the associated fan, if any, is on until the temperature reaches the desired value or 10° C. above the ambient temperature.

The computer system includes a gas pressure monitoring system to monitor the pressure of all input gas lines and inform the user accordingly. A dedicated system sets and maintains the set flow rate value for each gas. The valve/flow meter for each controlled flow rate operates in a closed loop. The set point is defined by the operator and maintained automatically.

An internal GPS module with antenna, preamplifier, and receiver may be used in some embodiments of the present invention to provide location position of the LPGC unit during field deployment. Positional information is stored with the instrument data and is available to the user through a status screen.

The ambient temperature is continuously monitored and the data used for control reference. The ambient temperature is considered to be the internal cabinet temperature of the LPGC, measured in the intake air plenum.

Figure 9:
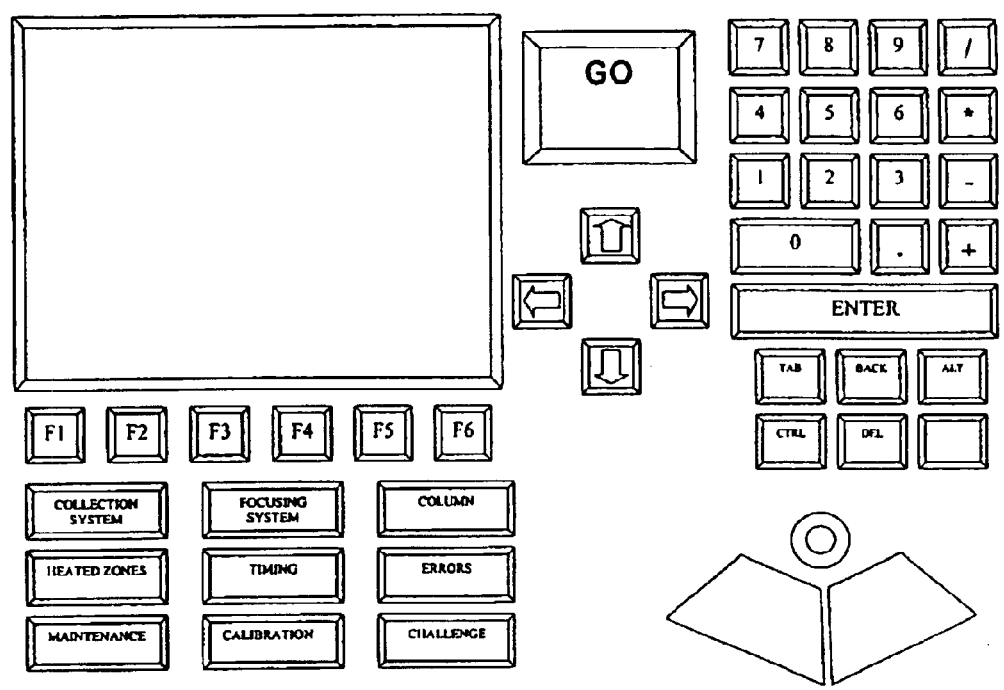
FIG. 9 is a proposed layout of the human interface of one embodiment of the present invention.

FIG. 9 shows the layout of one embodiment of the LPGC human interface 550 of the present invention. The precise layout, of course, may be varied without departing from the present invention. It is preferred, however, that the functionality of the layout is maintained as described below.

A display screen is provided that is preferably at least 4×5 inches and in color. Function keys 1 through 6 are context sensitive and the specific function of each key changes based on the window shown on the display screen. The "collection system" key displays the status and set points of the air collection system (collection tubes 110 and 120, valving, transfer lines, and collection flow rate). No illumination indicates that conditions are within acceptable parameters, and red illumination indicates that one or more values are outside of acceptable parameters.

The "focusing system" key displays the status and set points of the focusing system (focusing tube 146, valving, transfer lines). No illumination indicates that the conditions are within acceptable parameters, whereas red illumination indicates that one or more values are outside acceptable parameters. The "column" key displays the status and set points of analytical column 300 and carrier gas flow rate. Again, no illumination indicates that conditions are within acceptable parameters while red illumination indicates that one or more value is outside of acceptable parameters. The "heated zones" key displays the status and set points of injector 200, detector 400, and transfer lines within the LPGC system. The illumination scheme is the same as that described with respect to the other keys, above.

The "timing" key displays the set points for the instrument timing when operating. The "errors" key displays the instrument activity log. Yellow illumination indicates an error. The "GO" key is used to start a sample analysis. Green illumination indicates that all conditions within the LPGC are within acceptable parameters and analysis can proceed. The arrow keys allow movement of the cursor within a selected box displayed on the display screen. The number keys allow numeric entry of method parameters within selected fields on the display screen.

The "enter" key performs the normal Windows functions on the LPGC. The "maintenance" key commands the LPGC to go to the standby conditions. The standby conditions are listed in Table 3, below.

TABLE 3

| Subsystem | Condition |
|---|---|
| Injector Temperature | 50° C. |
| Transfer Line Temperature | 50° C. |

TABLE 3-continued

| Subsystem | Condition |
| --- | --- |
| Detector Temperature | 50° C. |
| Column Temperature | 40° C. |
| Air Sampler Valve Temperatures | 50° C. |
| Helium Flow Rate | 1.2 mL per minute |
| Air 1 Flow Rate | Off |
| Air 2 Flow Rate | Off |
| Hydrogen Flow Rate | Off |
| Ignitor Power | Off |

The "calibration" key is used to designate data files as "calibration". The "challenge" key places the instrument in challenge mode. Audio and visual alarms will be turned off and data will be denoted with this mode. The "tab" key allows cursor movement from one entry field to another in a predefined manner. The "back" key allows the cursor to be positioned back one space for each press within a selected entry field. The "alt," "ctrl," and "del" keys perform normal Windows functions on the LPGC. The mouse provides cursor movement and entry field selection using normal Windows functions.

What follows below is a general description of the functionality of various interface screens used in a preferred embodiment of the present invention. It should be noted that the specific details described below may be varied by those skilled in the art upon reading this disclosure.

It is preferred that a SECURITY screen be launched upon booting of the LPGC external computer. In a preferred embodiment of the present invention, this screen is simply the standard Windows 2000 user/password screen. Once the user name and password are authenticated, the modified EZChrom Elite software designed to be used with the present LPGC is launched. Following a period of inactivity, the computer will enter a sleep mode. The user will have to enter authentication information in order to access the LPGC after the sleep mode. This feature is part of the standard Windows 2000 security when using a password-protected screensaver.

In a preferred embodiment of the present invention, the first screen that the user will see following the SECURITY screen is the MODES screen. From this screen, the user will select liquid injection mode, single air sampling mode, continuous air sampling mode, or shut down mode. After selecting the appropriate method, the user is taken to the MAIN screen.

The MAIN screen for the LPGC allows the user to access all of the functions necessary to control the LPGC. Exiting the other functions of the LPGC returns the user to the MAIN screen. Navigation of the MAIN screen may be accomplished by using the "tab" key, the arrow keys, a mouse or the like. It is preferred that, from the MAIN screen, the user is able to start an analysis, download a method, tune the PFPD, load a stored set of historical data, enter a predefined list of sample names that the user can select during sample analysis, return to the MODES screen, or put the display into sleep mode.

If "Start Analysis" is chosen from the MAIN screen, the next screen displayed is an information entry screen in which the user is prompted to input information relevant to the sample before allowing the analysis process to begin. Information asked for by the device may include, but is not limited to:

1. A method name selectable by the user and associated with the current project. If the user does not select a method, the default is the last method run on the device.

2. A sample name selected from a drop-down list of pre-entered sample names entered during the method setup and calibration processes. Also the user can activate a pop-up virtual keyboard to enter a sample name that is not contained in the drop down list.

3. The current date and time. The LPGC system computer will already have the current date and time displayed to the user. It may be necessary to change the time and date values if they are inaccurate because the machine has been moved or because of some error, however this must be done from the Windows operating system itself.

4. The location of the sample, preferably as the meridian latitude and longitude coordinates of the device according to the onboard GPS location tracking system.

5. The classification of the sample. Examples of classifications that can be used include Top Secret, Secret, Unclassified, Confidential, and None.

6. Any applicable handling restrictions placed on data dealing with dissemination.

7. The name of the user initiating the sample process.

8. Sampling conditions such as the weather. This information may be gathered by use of a user-selectable field designating the general sampling conditions as Rain, Snow, Sleet, Fair, Mixed Precipitation, and others, for example.

9. The ambient temperatures in ° C. The temperature will be provided by the onboard ambient temperature sensor.

10. The job type, such as Verification, Screening, Emergency Response, and Perimeter Monitoring.

11. The sample type, such as Soil, Vegetation, Water, Wipe, Air, and Other.

12. A check box to be used to indicate that the user wants to print a custom report associated with the method after collection and analysis.

In addition to any or all of the above, keys can be used from this screen to return the user to the MAIN screen without saving the user's entries, to accept the user's entries and prepare the LPGC for analysis, and to allow the user to go to the collection edit screen to allow review of collection and analysis parameters.

During an analysis period, chromatograms are displayed on the screen in real time. The user is provided with the option of aborting the current run or sequence, displaying the LPGC column edit screen, or putting the display to sleep.

If the "tune" option is selected from the MAIN screen, the user is taken to the autotune screen. From the autotune screen there are preferably five options from which the user can select:

1. Start the autotune of the PFPD.
2. Abort or stop the autotune of the PFPD.
3. Choose to manually tune the PFPD.
4. Repeat an autotune of the PFPD.
5. Accept the tune parameters as part of the instrument setup and return to the MAIN screen.

It is preferred that the functionality above is associated with the interface's "function" keys, for example F1 through F5. The autotune screen also allows the user to set certain instrument parameters such as PFPD body temperature, the PFPD transfer line, the permeation tube default temperature, the permeation tube shut-off valve, high-voltage for the PMTs, the trigger value, the detector range, zero and attenuation of the PMTs, and the phosphorous and sulfur gates. This screen preferably does not allow the user to change the flow rates to the detector as that requires the selection of 'manual tune'.

If the user chooses to manually tune the PFPD, the user is able to set all of the parameters mentioned above with respect to the autotune screen, as well as the hydrogen and air flow rates and the number of revolutions on the fine adjust valve.

Various additional screens may be provided to allow the user to access and control the various LPGC subsystems. For instance, a screen which allows the LPGC operator to view the set point values, actual values, and associated error limits for the collection subsystem associated with the loaded method. Preferably, this screen is activated by pressing the "collection system" key on the LPGC keypad.

In a preferred embodiment of the present invention, pressing the "focusing system" key, or F2 from the collection screen, allows the user to access the focusing system screen. From there, the user can view the set point values, actual values and associated error limits for the focusing subsystem associated with the method that is loaded. Pressing the "column" button on the LPGC keypad allows the user to view the set point values, actual values and associated error limits for the LPGC column subsystem associated with the loaded method. The user can also edit the set point values and error limits. Pressing the "heated zone" key on the LPGC keypad brings the user to the heated zone screen. From this screen, the user can view the set point values, actual values and associated error limits for the LPGC heated zone subsystem associated with the loaded method.

Also provided is a timing screen, from which the LPGC user can view and edit the set point timing values for continuous air sampling associated with the loaded method. As noted above, the precise screens provided, as well as the layout and arrangement of the screens and the means by which they are accessed, may be modified by those skilled in the art without departing from the scope of the present invention.

In addition the user can connect a laptop computer and have access to all of the instrument and data analysis parameters and any stored data on the LPGC.

Operational Scenarios

The present device is designed to run under three different operational scenarios: 1) as a laboratory instrument; 2) as a first response/first entry monitor; and 3) as a stationary location monitor. Each scenario is described briefly below.

Laboratory Instrument

The LPGC of the present invention is designed to be used as a laboratory instrument on a day-to-day basis. The device can be used to screen soil, water, vegetation and debris sample extracts for a number of components, including the presence of chemical warfare residue. When being used as a laboratory instrument, it is assumed that the device will be in a stationary location and operate for days at a time. Normal laboratory resources are expected to be available when the device is operating under these conditions. For example, a source of gas and power is assumed to be available. The following description encompasses briefly the use of the present instrument as a laboratory instrument. The following description is exemplary and individual settings or steps may vary depending on the usage of the device.

Prior to initial use, the device is placed on a solid support surface such as a bench or table. Air, hydrogen and helium gas supplies are then attached to the external inlets on the LPGC and the gas supply selector on the instrument is positioned to select the external supply. An AC-DC converter is attached to the instrument, with the other end being plugged into the supply receptacle.

It is preferred that an external laptop or other computer is attached to the LPGC. The device will operate without the external computer, however the computer is necessary during data reanalysis and method setup and editing. The computer is booted and the modified version of EZChrom software, designed for use with the present device, is started.

The gas regulators of the LPGC are turned on and the pressure is adjusted to about 60 psi. Then, the power to the LPGC is also turned to the "on" position.

It is preferred that the Windows-based external computer prompt the user to enter a password prior to accessing the device. Once the password is entered, the EZChrom software will load and prompt the user to select the operating mode and method. Since the device is being used as a laboratory instrument, liquid injection mode should be selected.

When the PFPD has reached operating temperature, an autotune is performed to optimize the detector sensitivity. This is accomplished by selecting the "tune" option. The user can verify that the tune is correct by observing the sulfur emission on the display. Once the instrument is tuned it is ready to be used to analyze samples. At this point, the user selects "start analysis" from the main screen.

The instrument is calibrated according to protocol and applicable sample identification information is entered into the system by the user. The user then loads 1 $\mu$L of sample into a syringe and inserts the syringe into the injection port of the LPGC. The user then simultaneously depresses the syringe plunger and presses the "go" buttom on the LPGC human interface. The LPGC will show the analysis in real time and at the end of the operation the results will be displayed. These results can be printed if necessary. The user can repeat the analysis process until all samples are analyzed.

After all samples are analyzed, the device is placed in standby condition using the maintenance button on the LPGC human interface. At this point, the Windows operating system on the external computer can be shut down. Then the power switch to the LPGC should be set to the "off" position. Once the external computer is shut down properly, it can be disconnected from the LPGC and the AC power cord can be disconnected from the instrument and the supply receptacle. The gas regulators are then turned off and the pressure adjusted to 0 psi. The user may disconnect the air, hydrogen and helium gas supplies from the external inlets on the LPGC if the LPGC is to be moved, and the instrument can be packed safely into its shipping container.

First Response/First Entry Monitor

Before rescue or inspection personnel can safely enter an area of suspected terrorist action or agent production, their safety must be ensured. Gross level detectors are available that can indicate whether areas are free of agent concentrations that would cause personnel to immediate succumb to the agent's effects. Only instrumentation that is capable of detection at parts-per-billion (ppb) and parts-per-trillion (ppt) concentrations can provide assurance of safety for medium- and long-term exposures. The LPGC of the present invention can provide the required ppb and ppt level of detection with reasonable portability.

The following description encompasses briefly the use of the present instrument as a first response/first entry monitor. The following description is exemplary and individual settings or steps may vary depending on the usage of the device. In the exemplary description that follows, it is assumed that the LPGC will arrive at a staging area that allows personnel to function without wearing PPE. It is also assumed that limited support equipment is available and that external AC power may not be available.

First, the LPGC should be removed from its transport container and placed on a solid support surface such as a bench or table. Placement on the ground is also acceptable. It is assumed for purposes of this example that the instrument will be started in a location away from the environment where the air sampling is to be performed. For example, the instrument could be started on-board a vehicle en route to the location where it is to be used.

The user should verify that the on-board gas cylinders are fully charged or that sufficient gas is available for the required application. If there is not sufficient gas available, the user must refill or exchange the gas cylinders. The LPGC should be set to select the internal gas supply.

If an AC power supply is available, an AC-DC converter should be connected to the instrument with the other end being plugged into the supply receptacle. If AC power is not available, the instrument can be started on battery power. Starting the instrument on battery power will rapidly deplete the charge of the batteries and the batteries should be exchanged once the LPGC is allowed to warm up.

A laptop or other external computer should be attached to the LPGC and the LPGC power switch should be turned to the "on" position. Once the computer has booted, the user will preferably be prompted to enter a pass code in order to access the device. The modified EZChrom software will launch automatically and prompt the user to select the operational mode. The user should select single air sampling mode. Note that the laptop computer is not necessary for starting the low-power GC in any of the operational scenarios. It is only necessary for making changes to the method parameters.

When the PFPD has reached operating temperature, the user should perform an auto tune to optimize the detector sensitivity. This is accomplished by selecting "tune." The user can then verify that the tune is correct by observing the sulfur emission on the display. The user should then load the method to be used if it has not already been loaded.

The user then selects "start analysis" from the main screen and calibrates the instrument according to protocol. The laptop computer can then be disconnected from the LPGC and the LPGC can be transported to the area to be monitored.

Once the instrument arrives in the area to be monitored, the user presses the "go" key on human interface 550 to start sampling. The LPGC will show the analysis in real time. At the end, the results will be displayed if "single analysis" was selected. If "continuous" was selected, the instrument will continue to collect and analyze the surrounding air. Sampling can be continued for as long as necessary.

When sampling is complete, the GC should be moved to a safe area. The data collected can then be accessed, reviewed and printed as necessary. This can be accomplished using an external computer. Once use of the instrument is complete the LPGC can be placed into its standby condition using the maintenance button on the human interface. The power switch on the LPGC is then turned to the "off" position. If an external computer is attached to the LPGC it can be disconnected and the instrument returned to its transport container.

Stationary Location Monitor

The use of the LPGC as a stationary location monitor allows it to continuously monitor a location for the presence of chemical agents. It is contemplated that the instrument, or several instruments, can be positioned at designated locations for monitoring the perimeter of a chemical incident or as a continuous monitor during inspection of a hazardous area. The instruments transmit their data to a central command post where appropriate action can be taken if a chemical agent is detected. The actual operation of the device as a stationary location monitor is identical to that described under the first entry/first response monitor heading, above.

As is evident from the foregoing description, certain aspects of the present invention are not limited by the particular details of the examples illustrated herein, and it is therefore contemplated that other modifications and applications, or equivalents thereof, will occur to those skilled in the art. It is accordingly intended that the claims set forth below shall cover all such changes, modifications, variations and other uses and applications that do not depart from the spirit and scope of the present invention as described herein. Other aspects, objects and advantages of the present invention can be obtained from a study of the drawings, the disclosure and the appended claims.

What is claimed is:

1. A portable gas chromatograph comprising:
    an injector for delivering a sample to an analytical column associated with said chromatograph, said analytical column being in fluid communication with said injector,
    a detector in fluid communication with said analytical column for detecting the constituent components of the sample as they emerge from said analytical column;
    a computer system in electronic communication with said detector for hardware control and processing data generated by said gas chromatograph; and
    a housing for enclosing at least said analytical column, injector and detector, said housing having an interior wall wherein said analytical column, injector and detector are suspended from said interior wall, a plurality of shock insulation members coupled to said interior wall, said analytical column, injector and detector being insulated against shock applied to said portable gas chromatograph from more than one direction.

2. A portable gas chromatograph according to claim 1 wherein said detector is a pulsed-flame photometric detector.

3. A portable gas chromatograph according to claim 1 further comprising an onboard gas supply for providing at least one gas necessary for the operation of said portable gas chromatograph.

4. A portable gas chromatograph according to claim 1 further comprising an onboard power supply for providing power thereto.

5. A portable gas chromatograph according to claim 1 further comprising a second detector in fluid communication with said analytical column, said computer system being in electronic communication with said detector and said second detector, said computer system being adapted such that data from said detector can be compared with data from said second detector.

6. A portable gas chromatograph according to claim 1 further comprising a second analytical column in fluid communication with said injector, said detector being in fluid communication with said analytical column and said second analytical column, and said computer system being adapted such that data from said detector with respect to said analytical column can be compared with data from said detector with respect to said second analytical column.

7. A portable gas chromatograph according to claim 1 further comprising a second analytical column in fluid communication with said injector, and a second detector in fluid communication with said second analytical column, said computer system being in electronic communication with said second detector, said computer system being adapted such that data from said detector can be compared with data from said second detector.

8. A portable gas chromatograph according to claim 1 further comprising an air sampler module in communication with said injector, said air sampler module being adapted to continuously sample the ambient air.

9. A portable gas chromatograph according to claim 8 wherein said air sampler module is capable of sampling the ambient air at a rate of about 5 liters per minute.

10. A gas chromatograph comprising:
an injector for delivering a sample to a first analytical column associated with said chromatograph and a second analytical column associated with said chromatograph, said first analytical column and said second analytical column being in fluid communication with said injector;
a first detector in fluid communication with said first analytical column for detecting the constituent components of the sample as they emerge from said first analytical column;
a second detector in fluid communication with said second analytical column for detecting the constituent components of the sample as they emerge from said second analytical column;
a computer system in electronic communication with said detector and said second detector for hardware control and processing data generated by said gas chromatograph, said computer system being adapted such that data generated with respect to said first detector can be compared to data generated with respect to said second detector; and
a housing for enclosing at least said first and second analytical columns, said injector, and said first and second detectors, said housing including a sub module wherein said first and second analytical columns, said injector, and said first and second detectors are suspended within said sub module, a plurality of shock insulation members attached to said sub module, said first and second analytical columns, said injector, and said first and second detectors being insulated against shock applied to said portable gas chromatograph from more than one direction.

11. A gas chromatograph according to claim 10 wherein said first detector is a pulsed-flame photometric detector and said second detector is a pulsed-flame photometric detector.

12. A gas chromatograph according to claim 10 further comprising an onboard gas supply for providing at least one gas necessary for the operation of said portable gas chromatograph.

13. A gas chromatograph according to claim 10 further comprising an onboard power supply for providing power thereto.

14. A gas chromatograph according to claims 10 further comprising an air sampler module in communication with said injector, said air sampler module being adapted to continuously sample the ambient air.

15. A gas chromatograph according to claim 14 wherein said air sampler module is capable of sampling the ambient air at a rate of about 5 liters per minute.

16. A portable gas chromatograph comprising:
an injector for delivering a sample to an analytical column associated with said chromatograph, said analytical column being in fluid communication with said injector;
a detector in fluid communication with said analytical column for detecting the constituent components of the sample as they emerge from said analytical column;
a computer System in electronic communication with said detector for hardware control and processing data generated by said gas chromatograph;
an onboard gas supply for providing at least one gas necessary for the operation of said portable gas chromatograph; and
a housing for enclosing at least said analytical column, injector and detector, said housing including a sub module wherein said analytical column, said injector and said detector are suspended within said sub module, a plurality of shock insulation members attached to said sub module, said shock insulation members being the only points of contact between said sub module and said housing.

17. A portable gas chromatograph comprising:
an injector for delivering a sample to an analytical column associated with said chromatograph, said analytical column being in fluid communication with said injector,
a detector in fluid communication with said analytical column for detecting the constituent components of the sample as they emerge from said analytical column;
a computer system in electronic communication with said detector for hardware control and processing data generated by said gas chromatograph;
an onboard gas supply for providing at least one gas necessary for the operation of said portable gas chromatograph;
an onboard power supply to provide power thereto;
an air sampler module in communication with said injector, said air sampler module being adapted to continuously sample the ambient air, and
a housing for enclosing at least said analytical column, injector and detector, a rigid subframe attached to said analytical column, injector and detector, a plurality of shock insulation members attached to said rigid subframe, said shock insulation members insulating said analytical column, injector and detector against shock applied to said portable gas chromatograph.

18. A portable gas chromatograph comprising:
an injector for delivering a sample to a first analytical column associated with said chromatograph arid a second analytical column associated with said chromatograph, said first analytical column and said second analytical column being in fluid communication with said injector,
a first detector in fluid communication with said first analytical column for detecting the constituent components of the sample as they emerge from said analytical column;
a second detector in fluid communication with said second analytical column fir detecting the constituent components of the sample as they emerge from said second analytical column;
a computer system in electronic communication with said first and second detectors hardware control and processing data generated by said gas chromatograph, said computer system being adapted such that data generated with respect to said first detector can be compared to data generated with respect to said second detector;
an onboard gas supply for providing at least one gas necessary for the operation of said portable gas chromatograph;
an onboard power supply for providing power thereto:
an air sampler module in communication with said injector, said air sampler module being adapted to continuously sample the ambient air, and
a housing for enclosing a sub module, said sub module including at least said first and second analytical columns, said injector, and said first and second detectors, said sub module being secured to said housing, plurality of shock insulation members attached to said sub module, said shock insulation members being the only points of contact between said such module and said housing.

19. A portable gas chromatograph comprising:

in injector for delivering a sample to an analytical column associated with said chromatograph, said analytical column being in fluid communication with said injector, a detector in fluid communication with said analytical column for detecting the constituent components of the sample as they emerge from said analytical column;

a computer system in electronic communication with said detector for hardware control and processing data generated by said gas chromatograph;

a housing for enclosing at least said analytical column, injector arid detector, said housing having an interior wall;

a rigid subframe fixedly attached to at least said analytical column and detector, said rigid subframe having an upper surface;

a plurality of shock insulation members fixedly attached to the upper surface of said rigid subframe, said shock insulation members being the only points of contact between said rigid subframe and said housing.

20. The device of claim 19 wherein said shock insulation members are isolation bushings.

* * * * *

UNITED STATES PATENT AND TRADEMARK OFFICE
CERTIFICATE OF CORRECTION

PATENT NO.    : 6,837,096 B2
DATED         : January 4, 2005
INVENTOR(S)   : Douglas C. Stewart It is certified that error appears in the above-identified patent and that said Letters Patent is hereby corrected as shown below:

Column 4,
Lines 63-64, delete "Line 56 is an extension of the analytical column to the injector"

Column 10,
Line 1, delete "in" and replace with -- is --;
Line 4, delete "tow" and replace with -- low --;
Line 4, delete "U.S." and replace with -- use --;

Column 12,
Line 5, delete "tame" and replace with -- tune --;
Line 22, delete "tho" and replace with -- the --;
Line 25, delete "rote" and replace with -- rate --;
Line 28, delete "vanes" and replace with -- varies --;
Line 33, delete "cheek" and replace with -- check --;
Line 44, delete "tick-lock" and replace with -- tick-tock --;
Line 64, delete "readies" and replace with -- reaches --;
Lines 65 and 66, delete "alter" and replace with -- after --;

Column 13,
Line 7, delete "tick-tack" and replace with -- tick-tock --;
Line 23, delete "fines" and replace with -- lines --;
Line 51, Table 2, delete "Houseing" and replace with -- Housing --;

Column 24,
Line 21, delete "to provide" and replace with -- for providing --;
Line 32, after the word "portable" insert -- gas --;
Line 35, delete "arid" and replace with -- and --;
Line 46, delete "fir" and replace with -- for --;
Line 67, prior to the word "plurality", insert -- a --;

Column 25,
Line 5, prior to the word "injector", delete "in" and replace with -- an --;

UNITED STATES PATENT AND TRADEMARK OFFICE
CERTIFICATE OF CORRECTION

PATENT NO. : 6,837,096 B2
DATED : January 4, 2005
INVENTOR(S) : Douglas C. Stewart It is certified that error appears in the above-identified patent and that said Letters Patent is hereby corrected as shown below:

Column 26,
Line 2, delete "arid" and replace with -- and --

Signed and Sealed this

Nineteenth Day of April, 2005

JON W. DUDAS
*Director of the United States Patent and Trademark Office*